United States Patent [19]

Hafner et al.

[11] 4,029,641

[45] June 14, 1977

[54] PROCESS FOR THE SIMULTANEOUS OBTENTION OF INSULIN AND PANCREATIN FROM SWINE PANCREASES

[75] Inventors: Leonhard Hafner, Konigstein, Taunus; Wilhelm Schramm, Kelkheim, Taunus; Hans Kargl, Schwalbach, Taunus; Friedrich Kieser, Eppstein, Taunus, all of Germany

[73] Assignee: Hoechst Aktiengesellschaft, Frankfurt am Main, Germany

[22] Filed: Dec. 18, 1975

[21] Appl. No.: 641,927

[30] Foreign Application Priority Data

Dec. 20, 1974 Germany .......................... 2460334

[52] U.S. Cl. ...................... 260/112.7; 260/112.5 R
[51] Int. Cl.$^2$ ........................................ C07C 103/52
[58] Field of Search .................. 260/112.5 R, 112.7

[56] References Cited

UNITED STATES PATENTS

| | | | |
|---|---|---|---|
| 2,573,099 | 10/1951 | Frederiksen | 260/112.7 |
| 2,752,286 | 6/1956 | Schultz et al. | 260/112.7 |
| 2,779,706 | 1/1957 | Homan | 260/112.7 |
| 2,897,117 | 7/1959 | Romans | 260/112.7 |
| 3,720,657 | 3/1973 | deVries | 260/112.7 |

OTHER PUBLICATIONS

VanTruyen et al.: Chem. Abstr. 75:101214b (1971).

*Primary Examiner*—Delbert R. Phillips
*Attorney, Agent, or Firm*—Curtis, Morris & Safford

[57] ABSTRACT

A process for the simultaneous obtention of insulin and pancreatin from fresh or deep frozen swine pancreases by extracting the glands at a pH of about 5 to 7 with a reaction mixture containing at least 40% of acetone, separating the extracted substance and the remaining solids, instantly adjusting the solids to a pH of above 5.6 with a buffer, and then recovering insulin from the extraction mixture and pancreatin from the solids.

5 Claims, No Drawings

PROCESS FOR THE SIMULTANEOUS OBTENTION OF INSULIN AND PANCREATIN FROM SWINE PANCREASES

The present invention relates to a process for the simultaneous obtention of insulin and pancreatin from swine pancreases.

The pancreases of fattened beasts are interesting in two respects in their use as pharmaceutical crude substances. They are the one and only starting material for the obtention of insulin and, moreover, they contain valuable enzymes for a therapeutic application. Beef pancreases are important for the obtention of trypsin and chymotrypsin in addition to insulin, while swine pancreases permits obtaining the enzyme mixture pancreatin having lipolytic, amylolytic and proteolytic activities, which is a valuable therapeutic agent.

Because of the two functions described above and ever since pancreatic substances have been used in medicine, pharmacy and technique, every attempt has been made to obtain the two systems of active substances from a common starting material. The difficulties, however, in such a twin process arise from the fact that insulin is obtained under extraction conditions under which the enzymes are irreversibly inactivated for the greatest part. The complete extraction of the insulin is preferably effected under acid conditions — mostly pH 4 — in the presence of an organic solvent — mostly 50 – 80% by volume of ethanol. However, under these conditions, the amylases and lipases of the pancreas are not stable and are highly denatured.

The proteolytic system trypsin — chymotrypsin shows a better stability. The additional obtention of crystallized trypsin or a mixture of trypsin — chymotrypsin from the extraction residues of the insulin production is disclosed, for example in British Pat. No. 613,030, DBP No. 875,640, French Pat. No. 999,346, U.S. Pat. No. 2,686,148 and 2,751,330 or DBP No. 1,013,834.

In contradistinction thereto, the simultaneous obtention of insulin and pancreatin raises more problems. Because of the above difficulties, an economic process could not yet be found. German Pat. No. 745,284 describes a process in which the insulin is extracted in the alkaline pH range to protect the enzymes as far as possible. German Pat. Nos. 874,062 and 875,856 describe the acid extraction of insulin in which the enzymes are spared. However, in these processes too, the enzymes were impaired to such a degree that it is impossible to prepare a product under economic conditions complying with the current requirements.

In addition to the absolute pH ranges the process was carried out within, apparently, one of the main reasons for the considerable inactivation of the enzymes is the use of inorganic or organic acids to adjust the pH-value. This aspect is taken into consideration also in the process described in German Auslegeschrift No. 2,146,275 which discloses the obtention of insulin and pancreatin from lyophilised pancreatin. The insulin is extracted from the degreased, lyophilised glands using aqueous-organic solvents - preferably 60 – 80% ethanol - after addition of neutral salts, such as sodium chloride without directly adding acid. The extraction of insulin from fresh or deep frozen pancreases after adding salts such as sodium chloride or ammonium chloride has been described in U.S. Pat. No. 2,779,706.

All processes described have considerable drawbacks. One drawback is the too small yield of insulin, another one is the inactivation, almost entirely, of the enzymes, or, the last one is that technologically complicated and, hence, expensive operations such as lyophilisation have to be intercalated.

The present invention provides a process for the simultaneous obtention of insulin and pancreatin from fresh or deep frozen swine pancreases by the extraction of the glands in the presence of acetone, which process comprises using for the extraction a reaction mixture containing 40% of acetone at least and extracting at a pH of about 5 to 7, separating the solid from the extracted substance after the extraction, if desired after adding acetone once more, processing the extracted substance to obtain insulin in a manner known per se, adjusting the solid instantly with a buffer to a pH above 5.6 after its separation from the extraction mixture and processing the solid to pancreatin in a manner known per se.

The process of the invention permits overcoming the drawbacks of the known operational methods. Surprisingly, it has been found that the insulin can be extracted from fresh or deep frozen pancreases under fairly mild conditions when, to the glands cut into small pieces that are suspended in a mixture of water and acetone, the solution of a salt is added whose cations can react with components contained in the glands so that hydrogen-ions are set free from the reaction mixture. The hydrogen-ions cause a shift of the pH. For setting free the hydrogen ions, fatty acids forming undissociated compounds with metal ions are mainly involved. Suitable metal ions are especially those which are physiologically tolerable because it is generally unavoidable that residues of these salts remain in the pancreatin.

Less considered are, however, those metal ions, especially those heavy-metal ions, that impair the hormone or enzymatic activity of the final products. Preferred are water-soluble calcium salts, but magnesium, zinc, aluminum, iron, cobalt, nickel, tin and manganese salts may also be used. The necessary amount of salt to be added is determined by measuring the pH. Calcium salts, especially calcium chloride, are preferred, because of their good solubility and their physiological acceptability. A favorable side effect is the known enzyme-stabilizing property of the calcium ions.

For example, the addition of about 0.7% of calcium chloride to the small pieces of glands suspended in a mixture of acetone and water makes the pH of the mixture shift to 5 – 6, preferably to 5.4 – 5.6. Under these conditions, the sensitive enzymes of the pancreas suffer from a scarcely detectable deterioration. This effect can be intensified, if desired, by adding a suitable salt when the chemical reaction of this salt with the calcium salt sets the hydrogen-ions free. Suitable salts for this effect are acid salts of polybasic acids provided that the corresponding calcium salts formed in this reaction slightly dissociate under the given conditions or do not dissociate at all. For this purpose, for example, sodium dihydrogen-phosphate or disodium hydrogen-phosphate are suitable.

The addition of other neutral salts, such as sodium chloride or ammonium chloride and similar ones that are sometimes used for the extraction of insulin under different conditions, does not disturb these reactions and may be added.

The process of the invention can be carried out for example by cutting fresh or deep frozen swine pancreases into small pieces and suspending them in a mixture of, for example 24% by volume of water and 76% by volume of acetone, to which optionally the neutral salts and the salts of polybasic acids mentioned above have been added. For the extraction and the following separation of the undissolved gland constituents, it is advantageous to keep the concentration of the acetone in the liquid phase between 40 and 80% by volume, a condition that permits separation of the insulin from the gland tissue and impeding the activation of the zymogens which is caused by autolytic processes in the reaction mixture.

The volume of the extraction liquid is determined under practical aspects, so as are the sufficient dissolution of the active substance and the favorable technical handling of the suspension. Especially advantageous is an operational method in which the content of solid substance of the suspension is within the range of approximately 10 and 20%. This is the advantageous moment to add the calcium salt to the mixture, preferably in the form of an aqueous solution. The suspension brought to the desirable pH, which is advantageously within the range of 5 to 7, preferably 5.4 to 5.6, is stirred. When the usual stirring vessels are used, a sufficient extraction time is 0.5 to 1.5 hours. Then, the solid substances are separated, preferably by centrifuging. According to the invention, the solid substance can be extracted several times, but the number of the extractions should be restricted as far as possible to save the good quality of the pancreatin.

The clarified extracts are associated, if desired, and adjusted to a pH of 7 to 8, preferably 7.3 to 7.7, by adding alkaline solutions, advantageously diluted ammonia water, sodium hydroxide solution or an aqueous solution of a salt hydrolizing in an alkaline reaction, for example disodium-hydrogen phosphate. The inert protein fraction optionally flocculating out in this reaction can be centrifuged off. The limpid extract is adjusted to a pH in the acid range, freed from acetone under reduced pressure, degreased, the concentrate is precipitated in hydrochloric acid and the salt cake obtained is further processed to obtain insulin in a manner known per se.

The solid substance obtained after the separation of the insulin-containing extract is the starting material for pancreatin. In order not to damage the enzyme activities, the solid is instantly adjusted to pH 6 to 7 by adding a solution of a buffer salt or a mixture of buffer salts and is then further worked to obtain pancreatin in a manner known per se.

The following Examples illustrate the invention.

EXAMPLE 1

50 kg of deep frozen swine pancreases were cut into small pieces by means of a mincer and suspended at 15° C in a mixture of 120 l of acetone and 50 l of water. By adding an aqueous calcium chloride solution (100 g of calcium chloride in 150 ml of water), the pH-value was adjusted to 5.6. The mixture was stirred for 30 minutes at 15° C, 45 l of acetone were added and the solid was centrifuged off. The limpid phase contained the insulin; the solid was processed to pancreatin.

The solid was made into a paste with 40 l of an aqueous $Na_2HPO_4$-solution that contained as much phosphate as was necessary to adjust the pH to 6 to 6.5, and brought to an acetone content of 15% by distillation under reduced pressure at 25° C product temperature. Depending on the quality of the gland, the viscous distillation residue was maintained at 25° C during a period up to 3 hours, stirred with 250 ml of acetone and heated to 30° C.

The solid substance and the limpid phase were centrifuged off. The solid was extracted once more at 25° C with 150 l of acetone that contained 10 l of water, centrifuged off and dried at 25 °14 30° C under reduced pressure to conserve the activities of the enzymes.

Yield: 9 kg of pancreatin.

The insulin extract obtained from centrifugation was evaporated under reduced pressure until free from acetone. The precipitated grease was separated. The dissolved insulin was isolated from the aqueous distillation residue in a manner known per se.

Yield: 3 g of insulin having 25 I.U./mg = 75,000 I.U of insulin.

EXAMPLE 2

The mixture used for the extraction of insulin consists of 120 l of water in which 1 kg of ammonium chloride and 0.5 kg of primary sodium hydrogen-phosphate are dissolved.

The reaction mixtures and reaction conditions correspond to those indicated in the preceding Example 1. The yields are the same.

What is claimed is:

1. A method for treating fresh or deep frozen swine pancreases simultaneously to obtain therefrom an insulin-containing material and a pancreatin-containing material, which method comprises extracting said pancreases with an aqueous extractant containing at least 40 percent by volume of acetone and having dissolved therein a first soluble salt the cation of which reacts with acidic substances accompanying the insulin to form undissociated compounds therewith while releasing hydrogen ions therefrom to establish a pH of about 5 to 7 in the pancreas-extractant combination, separating the extract and remaining solids after the extraction, and instantly adjusting the pH of the resulting solids to a pH above 5.6 by combining them with a buffer, whereby the extract so obtained is an insulin-containing material from which insulin can be isolated and the solids so obtained are a pancreatin-containing material.

2. A method as in claim 1 wherein said aqueous extractant additionally has dissolved therein a second soluble salt which is an acid salt of a polybasic acid the anion of which reacts with the cation of said first soluble salt to form an undissociated compound therewith while releasing hydrogen ions therefrom also to establish a pH of about 5 to 7 in the pancreas-extractant combination.

3. A method as in claim 1 wherein said extractant contains between 40 and 80 percent by volume of acetone.

4. A method as in claim 1 wherein said first soluble salt is a salt of calcium, magnesium, zinc, aluminum, iron, cobalt, nickel, tin, or manganese.

5. A method as in claim 2 wherein said second soluble salt is sodium dihydrogen phosphate or disodium hydrogen phosphate.

* * * * *